United States Patent [19]

Breuer et al.

[11] 4,128,724
[45] Dec. 5, 1978

[54] HYDRAZINOCARBONYLAMINO CEPHALOSPORINS

[75] Inventors: Hermann Breuer; Uwe D. Treuner, both of Regensburg, Fed. Rep. of Germany

[73] Assignee: E. R. Squibb & Sons, Inc., Princeton, N.J.

[21] Appl. No.: 868,781

[22] Filed: Jan. 12, 1978

Related U.S. Application Data

[62] Division of Ser. No. 745,156, Nov. 26, 1976, Pat. No. 4,091,212.

[51] Int. Cl.$^2$ .................. C07D 501/36; C07D 501/56; C07D 501/32
[52] U.S. Cl. .......................................... 544/30; 544/4; 544/24; 544/25; 544/26; 544/27; 544/28
[58] Field of Search .................. 544/4, 25, 26, 27, 28, 544/30

Primary Examiner—Donald G. Daus
Assistant Examiner—David E. Wheeler
Attorney, Agent, or Firm—Lawrence S. Levinson; Merle J. Smith

[57] ABSTRACT

New α-hydrazinocarbonylamino cephalosporins which have the formula

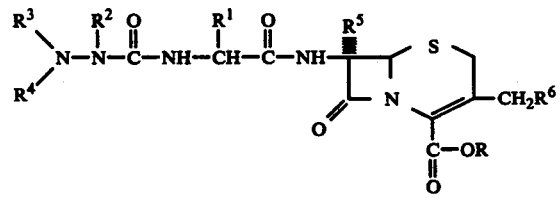

are useful as antimicrobial agents.

14 Claims, No Drawings

HYDRAZINOCARBONYLAMINO CEPHALOSPORINS

This is a division of application Ser. No. 745,156, Nov. 26, 1976, now U.S. Pat. No. 4,091,212.

SUMMARY OF THE INVENTION

This invention relates to new α-hydrazinocarbonylamino cephalosporins which have the formula

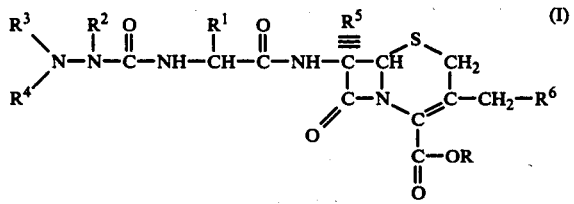

wherein

R is hydrogen, lower alkyl, phenyl-lower alkyl, diphenyhl-lower alkyl, trihaloethyl, tri(lower alkyl)-silyl, tri(lower alkyl)stannyl, or a salt forming ion;

$R^1$ is hydrogen, lower alkyl, saturated or unsaturated cycloalkyl, unsubstituted or substituted phenyl, thienyl, furyl or pyridyl;

$R^2$ and $R^3$ each is hydrogen or lower alkyl;

$R^4$ is hydrogen, lower alkyl, lower alkanoyl, halo-lower alkanoyl or unsubstituted or substituted cyanoacetyl;

$R^5$ is hydrogen or methoxy;

$R^6$ is hydrogen, lower alkanoyloxy, carbamoyloxy, lower alkoxy, unsubstituted or substituted pyridyl, or $-S-R^7$;

$R^7$ is lower alkyl or an unsubstituted or substituted five or six membered heterocyclic containing carbon nitrogen, sulfur or oxygen.

DETAILED DESCRIPTION OF THE INVENTION

This invention relates to α-hydrazinocarbonylamino cephalosporins which have the formula I above.

R is hydrogen, a salt forming ion or an ester group of the type described above. The salt forming ions include metal ions, e.g. aluminum, alkali metal ions like sodium or potassium, alkaline earth metal ions like calcium or magnesium, amine salt ions like cyclo-lower alkylamines such as cyclohexylamine, dicyclo-lower alkylamines such as dicyclohexylamine, lower alkylamines such as methylamine or ethylamine, tri-lower alkylamines such as triethylamine, etc. The ester groups include those mentioned, e.g. lower alkyl esters such as methyl, ethyl, propyl, butyl, t-butyl, etc., tri(lower alkyl)silyl such as trimethylsilyl or triethylsilyl, tri(lower alkyl)stannyl such as trimethylstannyl or triethylstannyl, trihaloethyl such as 2,2,2-trichloroethyl, diphenyl-lower alkyl such as diphenylmethyl and other easily removed ester groups.

The lower alkyl groups represented by R and the other symbols or part of other radicals like phenyl-lower alkyl are straight or branched chain hydrocarbon groups having up to seven carbons such as methyl, ethyl, propyl, isopropyl, butyl, sec-butyl, t-butyl or the like. The lower alkoxy groups are similar chains having up to seven carbons such as methoxy, ethoxy, propoxy, isopropoxy, etc. The $C_1-C_4$ and especially $C_1-C_2$ lower alkyl and lower alkoxy groups are are preferred. Preferred phenyl-lower alkyl groups are phenylmethyl and phenylethyl.

The cyclo-lower alkyl groups are the cycloaliphatic groups having up to six carbons and 0 to 2 double bonds, preferably the $C_4-C_6$ members and especially, cyclobutyl, cyclopentyl, cyclohexyl, cyclopentenyl, cyclohexenyl and 1,4-cyclohexadienyl.

The substituted phenyl groups are phenyl groups simply substituted with one halogen, lower alkyl or lower alkoxy group, preferably in the 4-position of the phenyl ring, e.g. 2-, 3- or 4-chlorophenyl, 2-, 3- or 4-bromophenyl, 2-, 3- or 4-methylphenyl, 2-, 3- or 4-methoxyphenyl and the like.

The heterocyclic groups represented by $R^1$ as well as those represented by $R^7$ can be attached in the 2-, 3- or 4-position, but the 2-position is preferred.

The lower alkanoyl groups are the acyl radicals of the lower fatty acids having up to seven carbons, e.g. acetyl, propionyl, butyryl, etc., with those having up to four carbons, and especially acetyl, being preferred. The lower alkanoyloxy groups are of the same type with acetyloxy being especially preferred. The halo-lower alkanoyl groups represented by $R^4$ are of the same type, but they can include one to three halogens. Preferably they are haloacetyl groups like chloroacetyl, bromoacetyl, dichloroacetyl, trichloroacetyl, trifluoroacetyl, etc., but others like 3-chloropropionyl are also included.

The halogens in the various foregoing groups are the four common halogens, but chlorine and bromine are preferred, especially chlorine.

The unsubstituted or substituted cyanoacetyl groups represented by $R^4$ have the structure

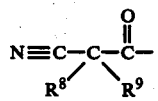

wherein $R^8$ and $R^9$ each is hydrogen or lower alkyl or $R^8$ and $R^9$ complete an alicyclic hydrocarbon ring like cyclopropyl, cyclobutyl, cyclopentyl or cyclohexyl, preferably cyclopropyl. Unsubstituted cyanoacetyl is especially preferred.

The substituted pyridyl group represented by $R^6$ is a pyridine ring bearing a carbamoyl group, preferably in the 4-position.

The heterocyclics represented by $R^7$ are five or six-membered nitrogen heterocyclics containing carbon and nitrogen and optionally an oxygen or sulfur atom. These are unsubstituted or substituted by a lower alkyl group. These include particularly tetrazoles, triazoles, thiazoles, thiadiazoles, oxadiazoles, oxazoles, and pyridine-N-oxides having the formulas

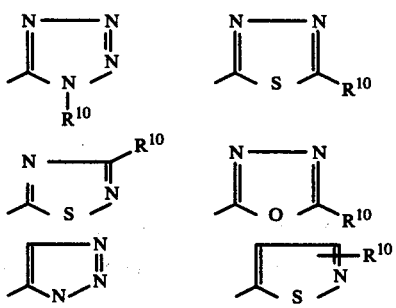

-continued

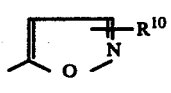 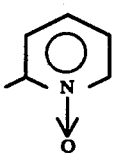

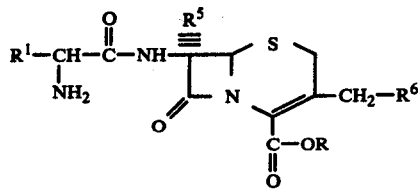

$R^{10}$ is hydrogen or lower alkyl, especially methyl.

The foregoing meanings for the various groups represented by the symbols have the same meanings throughout this specification and the illustrative groups named are preferred groups.

Especially preferred subgroups within the ambit of formula I are those wherein

R is hydrogen or alkali metal, especially hydrogen, sodium or potassium;

$R^1$ is phenyl, thienyl or hydrogen, especially the first two;

$R^2$ is hydrogen;

$R^3$ is hydrogen or lower alkyl, especially hydrogen or methyl;

$R^4$ is hydrogen, lower alkyl especially methyl, lower alkanoyl especially acetyl, or cyanoacetyl;

$R^5$ is hydrogen;

$R^6$ is hydrogen, lower alkanoyloxy especially acetoxy, or —S—$R^7$;

$R^7$ is 1-methyltetrazolyl.

The products of this invention can be produced by several alternative general methods described below. The examples which follow provide additional process details and illustrate the method generally preferred for producing the type of compound involved as well as serving as models for other members.

According to one method, a compound of formula I is produced by reacting a compound having the formula

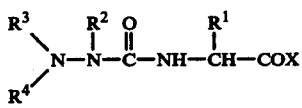

wherein X represents an activating group such as a halogen, preferably chlorine, mixed anhydride, activated ester, reaction product with a carbodiimide or other group conventional in such a reaction, with a 7-aminocephalosporanic acid derivative having the formula

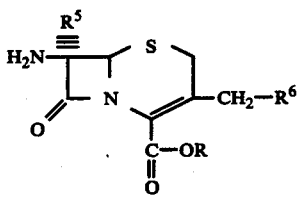

According to another method, a compound having the formula is made to react with a compound having the formula

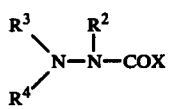

X in this instance is preferably chloro or phenylthio.

In the foregoing procedures R is preferably an easily removable protecting group. According to a preferred method R is a diphenylmethyl group which is removed after the coupling of the two reaction partners, e.g., by treatment with anisole and trifluoroacetic acid.

As a modification of the foregoing methods, compounds of formula I wherein $R^6$ is the sulfur containing group —S—$R^7$ can be produced from the corresponding compounds of formula I wherein $R^6$ is acetoxy. The latter is made by one of the methods described above, then this product is made to react with a thiol having the formula

HS—$R^7$       (VII)

Similarly, compounds of formula I wherein $R^6$ is unsubstituted or substituted pyridyl are made from the corresponding compound wherein $R^6$ is acetoxy by reaction with an unsubstituted or substituted pyridine of the formula

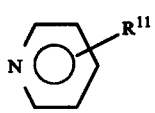

wherein $R^{11}$ is hydrogen or carbamoyl.

According to still another method, a compound of formula I wherein $R^4$ is hydrogen, e.g., having the formula

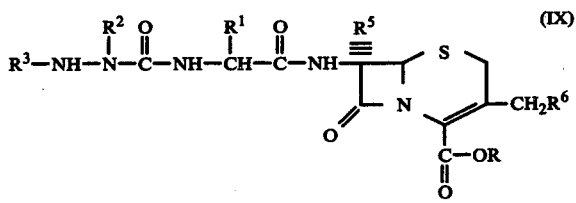

is acylated, e.g., with an acylating agent such as an acyl halide or acid anhydride, e.g., a lower alkanoyl halide or anhydride, a halo-lower alkanoyl halide or cyanoacetyl halide.

The compounds of formula I wherein $R^4$ is cyanoacetyl are preferably produced by first reacting an isocyanate compound having the formula

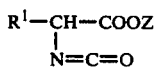 (X)

wherein Z is a protecting group like

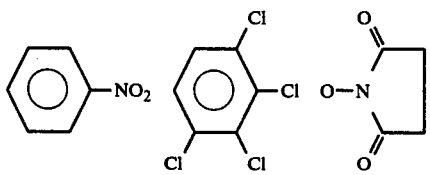

with a compound having the formula

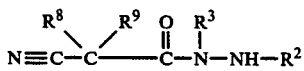 (XI)

to obtain an intermediate having the formula

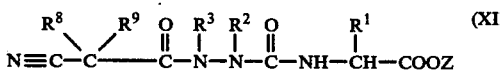 (XII)

The intermediate of formula XII is then made to react with the compound of formula IV as described above.

Another preferred modification for producing such compounds comprises reacting a compound having the formula

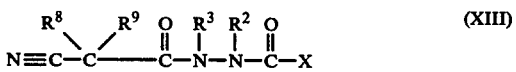 (XIII)

wherein X is halogen, preferably chlorine, with a compound of formula V as described above.

Other process steps, e.g., forming compounds wherein $R^6$ is pyridyl or $-S-R^7$, are the same as described above.

The asterisk in formula I indicates an asymmetric carbon. The products can therefore be obtained as racemic mixtures or in the form of the stereoisomers, all of which are within the scope of this invention. The products can be obtained by utilizing a starting material in the racemic form in which case the final product is racemic, whereupon separation of the stereoisomeric forms can be effected by conventional separation techniques. Alternatively, the D or L-form of the starting material can be used to produce the D or L-form of the final product directly. Generally, the D-isomer is preferred. The methoxy group, which can be present in the 7-position, is in the α-configuration.

The compounds of formula I have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Enterobacter cloacae, Klebsiella pneumoniae, Serratia marcescens*, etc. They can be used as antibacterial agents in a prophylactic manner or to combat infections due to organisms such as those named above, and in general may be utilized in a manner similar to cephradine and other cephalosporins. For example, a compound of formula I or a physiologically acceptable salt thereof can be used in various mammalian species such as mice, rats, dogs, etc., in an amount of about 1 to 100 mg/kg, daily, orally or parenterally, in single or two to four divided doses to treat infections of bacterial origin, e.g., 5.0 mg/kg in mice.

About 10 to 400 mg. of an acid compound of formula I or a physiologically acceptable salt thereof is incorporated in an oral dosage form such as tablet, capsule or elixir or in an injectable form in a sterile aqueous vehicle. The substance is compounded with a physiologically acceptable vehicle, excipient, binder, preservative, stabilizer, flavor, etc., in a unit dosage form as called for by accepted pharmaceutical practice. The amount of active substance in these compositions or preparations is such that a suitable dosage in the range indicated is provided.

The following examples are illustrative of the invention and constitute especially preferred embodiments. They also serve as models for the preparation of other members of the group which can be produced by suitable substitution of starting materials. All temperatures are in degrees celsius.

EXAMPLE 1

1.68 g. (0.022 mole) of acetylhydrazine are dissolved in 80 ml. of methylene chloride and 4.24 g. (0.02 mole) of DL-α-isocyanato-2-thiopheneacetic acid ethyl ester are added to the solution which is then stirred overnight. Crystals precipitate which are isolated to obtain 4.9 g. of DL-α-[[(2-acetylhydrazino)carbonyl]amino]-2-thiopheneacetic acid, ethyl ester as light crystals, m.p. 105°–112° (dec.).

EXAMPLE 2

4.6 g. of the product of Example 1 are stirred in 5.0 ml. of water and 24.5 ml. of 2N sodium hydroxide solution are added. As soon as a clear solution forms, it is acidified with dilute hydrochloric acid. The precipitate is filtered under suction to obtain 3.6 g. of DL-α-[[(2-acetylhydrazino)carbonyl]amino]-2-thiopheneacetic acid as light crystals, m.p. 171°–173° (dec.).

EXAMPLE 3

To a solution of 2.47 g. (0.005 mole) of 3-[[(1-methyl-1H-tetrazol-5-yl)thio]methyl]-7-aminocephalosporanic acid, diphenylmethyl ester in 30 ml. of methylene chloride is added a solution of 1.55 g. (0.006 mole) of DL-α-[[(2-acetylhydrazino)carbonyl]amino]-2-thiopheneacetic acid in 30 ml. of dimethylformamide. The mixture is cooled to 0°–5° and a solution of 1.16 g. (0.0055 mole) of dicyclohexylcarbodiimide in 10 ml. of methylene chloride is added dropwise. The mixture is stirred for 90 minutes at 0°–5° and 90 minutes at room temperature. This is then filtered, the filtrate is concentrated, the residue is dissolved in a mixture of ethyl acetate and tetrahydrofuran (2:1), the solution is washed with sodium bicarbonate and with water, concentrated and ether is added to the residue. The product, DL-7β-[[[[(2-acetylhydrazino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester is purified by dissolving in 70 ml. of tetrahydrofuran, 200 ml. of ethyl acetate are added and the mixture is concentrated to about 40 ml. 1.8 g. of product precipitates, which decomposes at 137°–175°.

EXAMPLE 4

1.6 g. of the product of Example 3 is permitted to react for 10 minutes at 0°–5° with 1.6 ml. of anisole and 50 ml. of trifluoroacetic acid. After concentrating and triturating with ether, 1.05 g. of DL-7β-[[[[(2-acetylhydrazino)carbonyl]amino]-2-thienylacetyl]amino]-3-[[1-methyl-1H-tetrazol-5-yl)thio]methyl]-8-oxo-5-thia-1-azabicyclo[4.2.0]oct-2-ene-2-carboxylic acid are obtained, m.p. 155°–160° (dec.).

EXAMPLE 5

0.5 g. of the product of Example 4 are dissolved in the equivalent amount of sodium bicarbonate in water and freeze-dried. 0.48 g. of DL-7β-[[[[(2-acetylhydrazino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt are obtained, m.p. 180°–205° (dec.).

EXAMPLE 6

By reacting D-α-isocyanato-2-benzeneacetic acid, ethyl ester with acetylhydrazine according to the procedure of Example 1, D-α-[[(2-acetylhydrazino)carbonyl]amino]benzeneacetic acid, ethyl ester is obtained as an amorphous product.

EXAMPLE 7

2.5 g. of the product of Example 6 are suspended in 10 ml. of ethanol and 13.7 ml. of 2N sodium hydroxide solution are added. After a clear solution forms, the alcohol is distilled off under vacuum and the aqueous phase is acidified with hydrochloric acid. 1.8 g. of D-α-[[(2-acetylhydrazino)carbonyl]amino]benzene acetic acid are obtained, m.p. 193°–195° (dec.).

EXAMPLE 8

The product of Example 7 and 7-aminocephalosporanic acid, diphenylmethyl ester are reacted according to the procedure of Example 3 to obtain D-7β-[[[[(2-acetylhydrazino)carbonyl]amino]phenylacetyl]amino]-3-[(acetyloxy)methyl]-8-oxo-5-thia-1-azabicyclo[4.2.0]oct-2-ene-2-carboxylic acid, diphenylmethyl ester, m.p. 180°–190° (dec.).

EXAMPLE 9

The product of Example 8 is treated with trifluoroacetic acid and anisole according to the procedure of Example 4 to obtain D-7β-[[[[(2-acetylhydrazino)carbonyl]amino]phenylacetyl]amino]-3-[(acetyloxy)methyl]-8-oxo-5thia-1-azabicyclo[4.2.0]oct-2-ene-2-carboxylic acid, m.p. 170°–185° (dec.).

EXAMPLE 10

0.35 g. of the product of Example 9 is brought into solution with an equivalent amount of sodium bicarbonate and the solution is freeze-dried to obtain 0.3 g. of D-7β-[[[[(2-acetylhydrazino)carbonyl]amino]-phenylacetyl]amino]-3-[(acetyloxy)methyl]-8-oxo-5-thia-1-azabicyclo[4.2.0]oct-2-ene-2-carboxylic acid, sodium salt.

EXAMPLE 11

A solution of 4.2 g. (0.02 mole) of DL-α-isocyanato-2-thiopheneacetic acid, ethyl ester and 1.2 g. (0.02 mole) of N,N-dimethylhydrazine in 80 ml. of methylene chloride is stirred overnight. The solution is concentrated and to the syrupy residue are added 10 ml. of 2N sodium hydroxide solution. After stirring for 30 minutes, a clear yellow solution results. By the addition of acetic acid, 3.9 g. of α-dimethylhydrazinocarbonylamino-2-thiopheneacetic acid are obtained, m.p. 208°–210°.

EXAMPLE 12

To 1.58 g. (0.0065 mole) of the product of Example 11 and 2.5 g. (0.005 mole) of 3-[[(1-methyl-1H-tetrazol-5-yl)thio]methyl]-7-aminocephalosporanic acid, diphenylmethyl ester in 80 ml. of dimethylformamide are added 1.13 g. (0.0055 mole) of dicyclohexylcarbodiimide dissolved in 15 ml. of tetrahydrofuran according to the procedure of Example 3. The product is similarly worked up to obtain 3.2 g. of crude 7β-[[DL-[[(2,2-di methylhydrazino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester which is purified by precipitating from ethyl acetate/ether, m.p. 109°–115° (dec.).

EXAMPLE 13

2.1 g. of the product of Example 12 are treated with trifluoroacetic acid and anisole according to the procedure of Example 4 to obtain 7β-[[DL-[[(2,2-dimethylhydrazino)carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, which is purified by dissolving in sodium bicarbonate solution and precipitating with hydrochloric acid, yield 0.6 g., m.p. 142°–152° (dec.).

EXAMPLE 14

9 g. (30 mmoles) of D-α-isocyanato-2-benzeneacetic acid, p-nitrophenyl ester and 3.6 g. of hydrazinoformic acid-t-butyl ester are stirred at 0° in 50 ml. of ether. After evaporating the solvent, the product α-[[[[(1,1-dimethylethoxy)carbonyl]hydrazino]carbonyl]amino]-benzene acetic acid, 4-nitrophenyl ester remains as a viscous honey-like mass which is crystallized by triturating with petroleum ether, m.p. 58°.

EXAMPLE 15

4.2 g. (10 mmoles) of the product of Example 1 are dissolved in 50 ml. of dimethylacetamide, 5 g. (10 mmoles) of 3-[[(1-methyl-1H-tetrazol-5-yl)thio]methyl]-7-aminocephalosporanic acid, diphenylmethyl ester and 10 mmoles of N-hydroxybenzotriazole are added and the mixture is stirred for 12 hours at 10°. The reaction mixture is then poured into 300 ml. of water and extracted with ethyl acetate. The ethyl acetate solution is washed once with sodium bicarbonate solution and twice with water, dried and concentrated. The residue is reprecipitated from methylene chloride/petroleum ether to obtain 7β-[[[[[[(1,1-dimethylethoxy)carbonyl]hydrazino]-carbonyl]amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester as a cream colored compound, m.p. 85°, yield 4.2 g.

EXAMPLE 16

5.5 g. of the product of Example 15 are stirred with 30 ml. of a mixture of trifluoroacetic acid and anisole (4:1) at −5°. The trifluoroacetic acid and anisole are distilled off from the clear solution and 20 ml. of ether are added to obtain 3 g. of a solid trifluoroacetic acid salt of 7β-[[[(hydrazinocarbonyl)amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid. This is dissolved in water, filtered and adjusted to pH 8 with dilute ammonia. On acidifying to pH 5.5 with 2N hydrochloric acid free 7β [[[hydrazinocarbonyl)amino]- phenylacetyl]amino]-3-[[(1-methyl-1H-tetrazol-5-yl)thio]methyl]-8-oxo-5-thia-1-azabicyclo[4.2.0]oct-2-ene-2-carboxylic acid precipitates. The product is filtered, dried and recrystallized from tetrahydrofuran/ether, yield 1,3 g., m.p. 140° (dec.).

The potassium salt is obtained as a beige powder by freeze-drying an equimolar aqueous solution of the acid and potassium bicarbonate, m.p. 288° (dec.).

EXAMPLE 17

168.16 g. (0.5 mole) of [[α-(4-methylbenzyloxy)carbonyl]amino]-2-thiopheneacetic acid are dissolved in 700 ml. of absolute tetrahydrofuran, 70 g. (0.5 mole) of p-nitrophenol are added and 103 g. (0.5 mole) of dicyclohexylcarbodiimide dissolved in 200 ml. of tetrahydrofuran are added dropwise with stirring at −10°. The mixture is stirred for 24 hours and the dicyclohexylurea which has formed is filtered off. The filtrate is treated with charcoal and the solvent is evaporated. The residual yellow oil crystallizes upon the addition of petroleum ether to yield D-[[α-(4-methylbenzyloxy)carbonyl]amino]-2-thiopheneacetic acid, 4-nitrophenyl ester as beige crystals, m.p. 82°-84°.

EXAMPLE 18

The product of Example 17 is added to 600 ml. of 6N hydrochloric acid in glacial acetic acid and stirred for 10 minutes at 10°. After evaporating the acetic acid in vacuo and washing the residue with ether, the D-2-thienylglycine-4-nitrophenyl ester, hydrochloride remains as a light gray powder, m.p. 170°-172°.

EXAMPLE 19

90 g. of the hydrochloride from Example 18 are suspended in 500 ml. of absolute toluene and a strong stream of phosgene is passed in while refluxing. After 1 hour, a clear solution forms. The solution is stirred for an additional half hour. After evaporating the solvent first under water pump vacuum and then through an oil pump, the product D-α-isocyanato-2-thiopheneacetic acid, 4-nitrophenyl ester remains as a brown oil which crystallizes after several days as a beige powder, m.p. 123°-124°.

EXAMPLE 20

4.5 g. (15 mmoles) of the product of Example 19 are dissolved in 50 ml. of tetrahydrofuran and 1.5 g. of cyanoacetic acid hydrazide suspended in 50 ml. of tetrahydrofuran are added at −20°. The mixture is stirred for 16 hours. The slightly turbid solution is then filtered, treated with charcoal and evaporated in vacuo. The product remains as a beige solid foam which is purified by dissolving in a little tetrahydrofuran and adding benzene until it becomes slightly turbid whereupon crystallization begins. The product, D-α-[[[2-(cyanoacetyl)hydrazino]carbonyl]amino]-2-thiopheneacetic acid, 4-nitrophenyl ester is obtained as light crystals, m.p. 132°-135°, yield 4.0 g.

EXAMPLE 21

5 g. (10 mmoles) of 3-[[(1-methyl-1H-tetrazol-5-yl)thio]methyl]-7-aminocephalosporanic acid, diphenylmethyl ester are dissolved in 60 ml. of dimethylacetamide and 4.03 g. (10 mmoles) of the nitrophenyl ester of Example 20 together with 1.35 g. (10 mmoles) of N-hydroxybenzotriazole are added. The mixture is stirred for 10 hours at 5° and 4 hours at room temperature. The reaction mixture is poured into 300 ml. of water and vigorously stirred for 10 minutes. It is then extracted with 3 × 100 ml. of ethyl acetate. The combined organic phases are washed with 3 × 100 ml. of water until no more yellow color of p-nitrophenol appears in the aqueous phase. The ethyl acetate phase is then dried, treated with charcoal and concentrated to obtain 5.1 g. of the product, D-7β-[[[[2-(cyanoacetyl)hydrazino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, as a beige powder, m.p. 168°.

EXAMPLE 22

4 g. of the product of Example 21 in a mixture of 30 ml. of trifluoroacetic acid and anisole (4:1) is stirred for 10 minutes at 0°. After distilling off the trifluoroacetic acid and anisole under vacuum, there is obtained a brown honey-like material which solidifies upon treatment with ether. The residue is purified by dissolving in sodium bicarbonate solution, filtering, acidifying the filtrate to pH 3.5 with 2N hydrochloric acid, whereupon the product precipitates in the form of a beige powder. The precipitate is dried over phosphorus pentoxide and reprecipitated from tetrahydrofuran/ether to obtain D-7β-[[[[2-(cyanoacetyl)hydrazino]carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, yield 2.3 g. of light powder, m.p. 152° (dec.).

EXAMPLE 23

The potassium salt of the product of Example 23, in the form of the monohydrate is obtained by freeze-drying an equimolar aqueous solution of the acid of Example 22 and potassium bicarbonate, light beige powder, m.p. 178° (dec.).

The following additional products are obtained by the procedures of the foregoing examples by reacting the substituted starting materials A and B having the substituents in the table to obtain the product C having those same substituents:

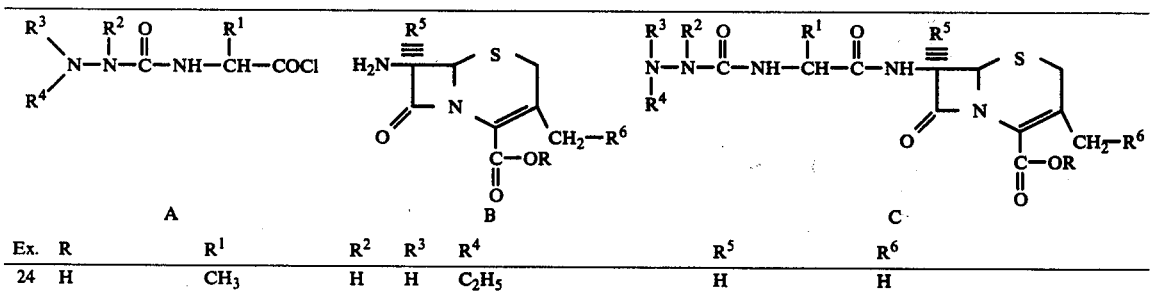

| Ex. | R | $R^1$ | $R^2$ | $R^3$ | $R^4$ | $R^5$ | $R^6$ |
|---|---|---|---|---|---|---|---|
| 24 | H | $CH_3$ | H | H | $C_2H_5$ | H | H |

-continued

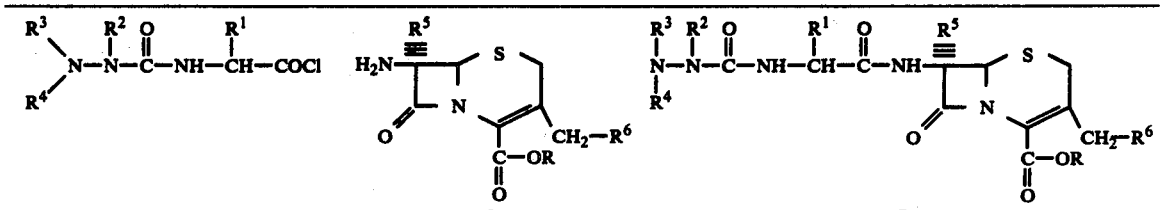

| Ex. | R | R¹ | R² | R³ | R⁴ | R⁵ | R⁶ |
|---|---|---|---|---|---|---|---|
| 25 | Na | H | $CH_3$ | $CH_3$ | $CH_3$ | H | $-OCOCH_3$ |
| 26 | H | H | $C_2H_5$ | H | H | H | $-S-CH_3$ |
| 27 | $C_2H_5$ | H | H | H | $-COC_2H_5$ | H | $-OCOCH_3$ |
| 28 | H | phenyl | H | H | $-COCH_3$ | $-OCH_3$ | -S-(1-methyl tetrazol-5-yl ... tetrazole) |
| 29 | H | 2-thienyl | H | H | $-COCH_3$ | $-OCH_3$ | -S-(5-methyl-1,3,4-oxadiazol-2-yl) |
| 30 | H | phenyl | $CH_3$ | H | $CH_3$ | H | -S-(1,3,4-thiadiazol-2-yl) |
| 31 | H | 2-thienyl | H | H | $-COC_3H_7$ | $-OCH_3$ | -S-(4-methyl-thiazol-2-yl) |
| 32 | H | phenyl | H | H | $-COCH_3$ | $-OCH_3$ | -S-(1-methyl-1H-tetrazol-5-yl) |
| 33 | K | 2-thienyl | H | H | $-COCH_3$ | $-OCH_3$ | -S-(1-methyl-1H-tetrazol-5-yl) |
| 34 | K | phenyl | H | $CH_3$ | $CH_3$ | $-OCH_3$ | -S-(1-methyl-1H-tetrazol-5-yl) |
| 35 | H | 2-thienyl | H | $CH_3$ | $CH_3$ | $-OCH_3$ | -S-(1-methyl-1H-tetrazol-5-yl) |
| 36 | H | phenyl | H | H | H | $-OCH_3$ | -S-(1-methyl-1H-tetrazol-5-yl) |
| 37 | Na | 2-thienyl | H | H | H | $-OCH_3$ | -S-(1-methyl-1H-tetrazol-5-yl) |

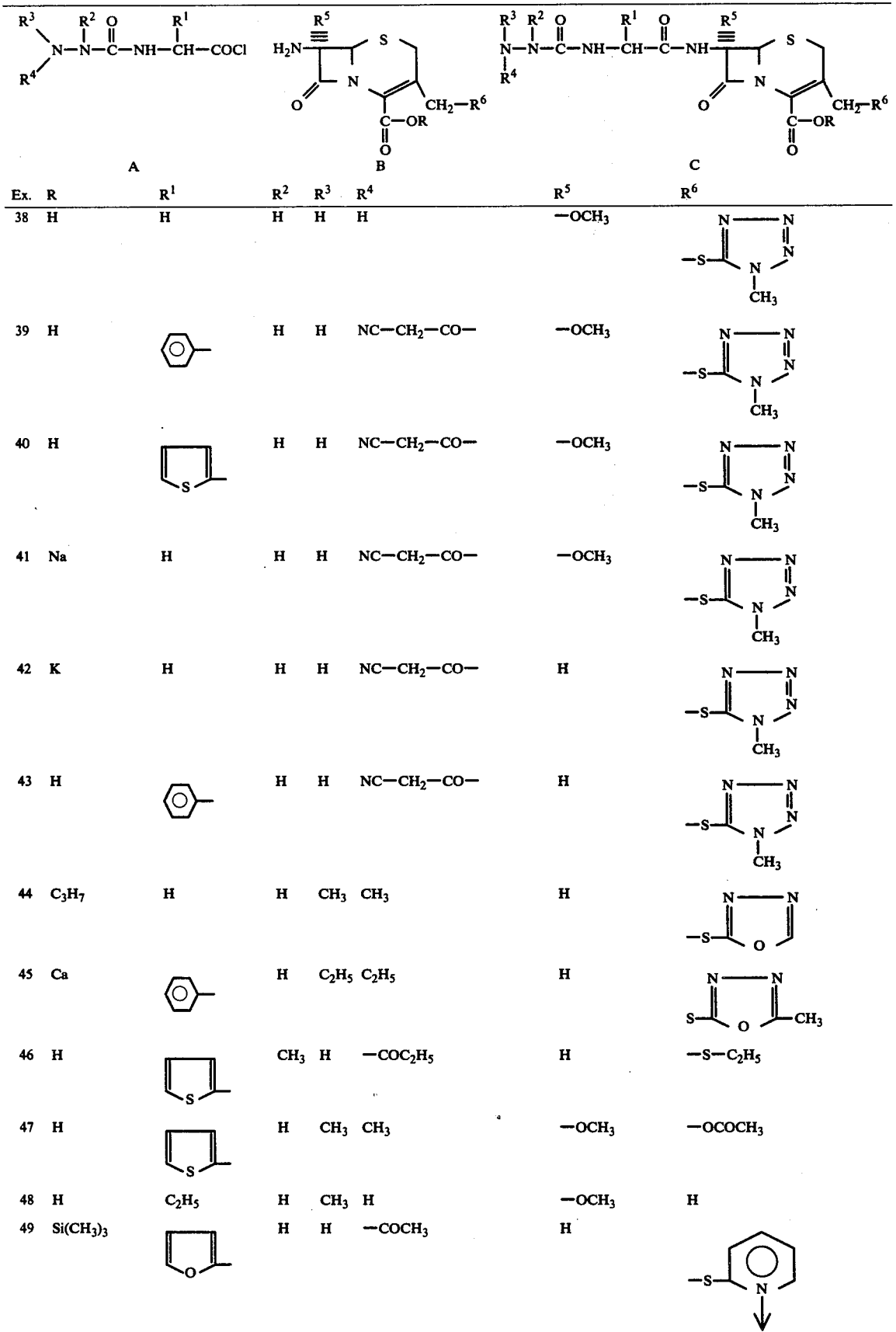

-continued

| | A | | | B | | | C | |
|---|---|---|---|---|---|---|---|---|
| Ex. | R | R¹ | R² | R³ | R⁴ | R⁵ | R⁶ |
| 50 | PhCH₂— | Ph— | H | H | H | H |  (isoxazolyl-S—) |
| 51 | (Cl₃)CCH₂— | 2-thienyl | CH₃ | H | CH₃ | | H |
| 52 | Sn(CH₃)₃ | H | H | H | NC—CH₂—CO— | H | —OCOCH₃ |
| 53 | H | cyclopentyl | CH₃ | H | H | H | H |
| 54 | Na | cyclohexyl | H | CH₃ | CH₃ | —OCH₃ | —S—CH₃ |
| 55 | H | cyclohexyl | H | H | —COCH₃ | H | —OCOCH₃ |
| 56 | H | cyclobutyl | H | H | —COCH₃ | H | —OCOCH₃ |
| 57 | H | Ph— | H | CH₃ | CH₃ | H | —OCOCH₃ |
| 58 | H | Ph— | H | H | —COCH₃ | H | —S—(1-methyl-1,2,4-triazolyl) |
| 59 | Na | Ph— | H | H | H | —OCH₃ | —S—CH₃ |
| 60 | H | Ph— | CH₃ | H | NC—CH₂—CO— | H | —S—(1-methyl-tetrazolyl) |
| 61 | H | Ph— | H | H | NC—CH₂CO— | —OCH₃ | —S—(1-methyl-tetrazolyl) |
| 62 | K | Ph— | H | H | —COCH₃ | —OCH₃ | H |
| 63 | H | cyclohexyl | H | H | —COCH₃ | H | —OCH₃ |
| 64 | H | 2-thienyl | H | H | H | —OCH₃ | —OC₂H₅ |
| 65 | H | Ph— | H | H | —COCH₃ | H | —OCONH₂ |

-continued

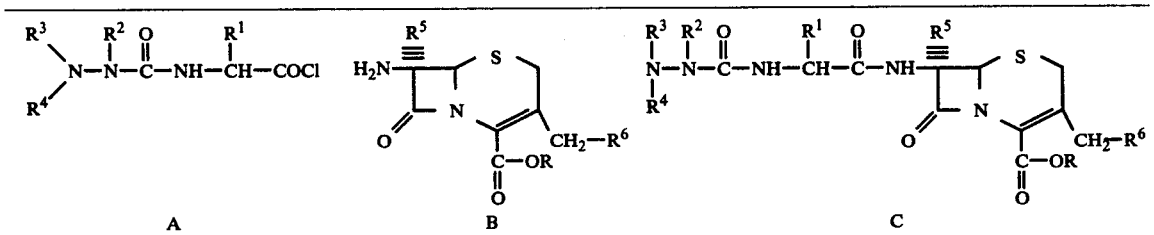

| | A | | B | | | C | |
|---|---|---|---|---|---|---|---|
| Ex. | R | R¹ | R² | R³ | R⁴ | R⁵ | R⁶ |
| 66 | H | 2-thienyl | H | CH₃ | CH₃ | —OCH₃ | —OCONH₂ |
| 67 | H | H | H | H | C₂H₅ | H | 2-pyridyl |
| 68 | H | phenyl | H | CH₃ | CH₃ | H | 4-carbamoyl-2-pyridyl |
| 69 | H | H | H | H | NC—C(piperidine ring)—CO— | H | —OCOCH₃ |
| 70 | Na | phenyl | H | H | NC—CH(CH₃)—CO— | —OCH₃ | —S-(1-methyl-tetrazol-5-yl) |
| 71 | H | 2-thienyl | H | H | NC—C(CH₃)₂—CO— | H | H |
| 72 | H | H | H | H | NC—C(cyclopropyl)—CO— | H | —OCOCH₃ |
| 73 | H | phenyl | H | H | NC—C(cyclopropyl)—CO— | —OCH₃ | —S-(1-methyl-tetrazol-5-yl) |
| 74 | H | 2-pyridyl | H | H | —COCH₃ | H | —OCOCH₃ |
| 75 | H | 4-chlorophenyl | H | CH₃ | CH₃ | H | —S-(1H-triazol-5-yl) |
| 76 | Na | 4-methoxyphenyl | H | H | H | H | —S-(1-methyl-triazol-5-yl) |
| 77 | H | H | H | H | ClCH₂CO— | H | —S—C₂H₅ |

-continued

Structure A:
$$R^3R^2\text{N-N}(R^4)-\text{C}(=O)-\text{NH-CH}(R^1)-\text{COCl}$$

Structure B:
$$H_2N-\text{[β-lactam-thiazine]}-\text{CH}_2-R^6, \text{ with } R^5 \text{ and } -C(=O)-OR$$

Structure C:
$$R^3R^2\text{N-N}(R^4)-\text{C}(=O)-\text{NH-CH}(R^1)-\text{C}(=O)-\text{NH-[β-lactam-thiazine]}-\text{CH}_2-R^6$$

| Ex. | R | $R^1$ | $R^2$ | $R^3$ | $R^4$ | $R^5$ | $R^6$ |
|---|---|---|---|---|---|---|---|
| 78 | H | thienyl | H | H | NC—CH$_2$—CO— | —OCH$_3$ | pyridyl-N-oxide |
| 79 | H | 4-methylphenyl | CH$_3$ | H | —COCH$_3$ | H | —S-(thiadiazole)-S- |
| 80 | H | thienyl | H | CH$_3$ | CH$_3$ | —OCH$_3$ | —S-(thiadiazole)-S-CH$_3$ |
| 81 | H | H | H | H | H | H | —S-(thiazole) |
| 82 | H | phenyl | H | H | NC—CH$_2$—CO— | H | —S-(methylthiazole) |

What is claimed is:

1. A compound of the formula $$R^3R^2\text{N-N}(R^4)-\text{C}(=O)-\text{NH-CH}(R^1)-\text{C}(=O)-\text{NH-[β-lactam]}-\text{CH}_2-R^6$$

with $R^5$ substituent and $-C(=O)-OR$ group wherein

R is hydrogen, lower alkyl, phenyl-lower alkyl, diphenyl-lower alkyl, trihaloethyl, tri(lower alkyl)-silyl, tri(lower alkyl)stannyl or a salt forming ion of the group consisting of aluminum, alkali metal, alkaline earth metal, cyclo-lower alkylamine, dicyclo-lower alkylamine and lower alkylamine;

$R^1$ is hydrogen, lower alkyl, thienyl, furyl, pyridyl, cyclobutyl, cyclopentyl, cyclohexyl, cyclopentenyl, cyclohexenyl, cyclohexadienyl, phenyl, mono-substituted phenyl wherein the phenyl substituent is halo, lower alkyl or lower alkoxy, $R^2$ and $R^3$ each is hydrogen or lower alkyl;

$R^4$ is hydrogen, lower alkyl, lower alkanoyl, halo-lower alkanoyl, cyanoacetyl or substituted cyanoacetyl wherein the cyanoacetyl substituent is lower alkyl or cyclo-lower alkyl;

$R^5$ is hydrogen or methoxy;

$R^6$ is hydrogen, lower alkanoyloxy, pyridyl, substituted pyridyl wherein the pyridyl substituent is carbamoyl, or —S— pyridyl-N-oxide.

2. A compound as in claim 1 wherein $R^1$ is phenyl.
3. A compound as in claim 1 wherein $R^1$ is thienyl.
4. A compound as in claim 1 wherein $R^1$ is hydrogen.
5. A compound as in claim 1 wherein $R^3$ and $R^4$ each is hydrogen.
6. A compound as in claim 1 wherein $R^3$ and $R^4$ each is lower alkyl.
7. A compound as in claim 1 wherein $R^3$ is hydrogen and $R^4$ is lower alkanoyl.
8. A compound as in claim 1 wherein $R^3$ is hydrogen and $R^4$ is cyanoacetyl.
9. A compound as in claim 1 wherein $R^5$ is hydrogen.
10. A compound as in claim 1 wherein $R^5$ is methoxy.
11. A compound as in claim 1 wherein $R^6$ is acetoxy.
12. A compound as in claim 1 wherein R is hydrogen or alkali metal; $R^1$ is hydrogen, phenyl or thienyl; $R^2$ and $R^5$ each is hydrogen; $R^3$ is hydrogen or lower alkyl; $R^4$ is hydrogen, lower alkyl, lower alkanoyl or cyanoacetyl; $R^6$ is hydrogen or lower alkanoyloxy.
13. A compound as in claim 1 wherein R, $R^2$, $R^3$ and $R^5$ each is hydrogen.
14. A compound as in claim 13 wherein $R^1$ is phenyl, $R^4$ is acetyl, and $R^6$ is acetoxy.

UNITED STATES PATENT AND TRADEMARK OFFICE
CERTIFICATE OF CORRECTION

PATENT NO. : 4,128,724
DATED : December 5, 1978
INVENTOR(S) : Hermann Breuer, Uwe D. Treuner It is certified that error appears in the above-identified patent and that said Letters Patent are hereby corrected as shown below:

In the Abstract in the formula $R^5$ should be attached by a triple bond --
Column 1, line 22 "phenyhl" should read -- phenyl --
Column 1, line 68 delete "are" second occurrence
Column 2, line 68, third formula in the first column should be

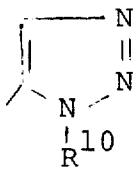

Column 5, in the second group of formulas, the middle formula should read

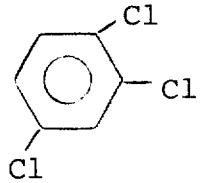

Column 7, line 47 insert a hyphen between "5" and "thia".

Signed and Sealed this

Thirteenth Day of January 1981

[SEAL]

Attest:

SIDNEY A. DIAMOND

Attesting Officer    Commissioner of Patents and Trademarks